US005773223A

United States Patent [19]

Shyamala et al.

[11] Patent Number: 5,773,223

[45] Date of Patent: Jun. 30, 1998

[54] ENDOTHELIN $B_1$, ($ETB_1$) RECEPTOR POLYPEPTIDE AND ITS ENCODING NUCLEIC ACID METHODS, AND USES THEREOF

[75] Inventors: Venkatakrishna Shyamala, Oakland; Patricia Tekamp Olson, San Anselmo, both of Calif.

[73] Assignee: Chiron Corporation, Emeryville, Calif.

[21] Appl. No.: 117,361

[22] Filed: Sep. 2, 1993

[51] Int. Cl.[6] .............................. C12Q 1/00; C12N 15/12; C07K 14/705

[52] U.S. Cl. .......................... 435/7.2; 435/69.1; 530/350; 536/23.5

[58] Field of Search .................................... 435/69.1, 7.1, 435/7.2, 7.21; 530/350; 536/23.5

[56] References Cited

PUBLICATIONS

Nakamuta et al., *BioChem. and Biophys. Res. Comm.* (1991) 177:34–39.

Ogawa et al., *BioChem. and Biophys. Res. Comm.* (1991) 178:248–255.

Sakamoto et al., *BioChem. and Biophys. Res. Comm.* (1991) 178:656–663.

Mizuno et al., *Biochem. J.* (1992) 287:305–309.

Arai et al., *J. of Biological Chem.* (1993) 268:3463–3470.

Adachi et al., FEBS, vol. 311, p. 179, 1992.

Aramori et al., The Journal of Biological Chemistry, vol. 267, p. 12468, 1992.

*Primary Examiner*—Stephen Walsh
*Assistant Examiner*—Sally P. Teng
*Attorney, Agent, or Firm*—Ling-Fong Chung; Grant D. Green; Robert P. Blackburn

[57] ABSTRACT

A new endothelin B receptor has been identified, and the amino acid and nucleotide sequence of the receptor are provided. The nucleotide sequence is useful to construct expression cassettes and vectors to produce host cells which are capable of expressing the receptor, its mutants, fragments, or fusions. Such polypeptides are useful for identifying new endothelin agonists and antagonists.

2 Claims, No Drawings

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 452 amino acids
( B ) TYPE: amino acid
( C ) STRANDEDNESS: single
( D ) TOPOLOGY: linear ( i x ) FEATURE:

( A ) NAME/KEY: -
( B ) LOCATION: 199..208
( D ) OTHER INFORMATION: /note= "Decapeptide Insert"

( x i ) SEQUENCE DESCRIPTION: SEQ ID NO:1:

```
Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
        115                 120                 125

Asn Lys Cys Met Arg Asn Gly Pro Asn Ile Leu Ile Ala Ser Leu Ala
    130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190

Cys Ala Leu Ser Ile Asp Ser Leu Lys Tyr Asn Ser Ile Phe Ile Phe
        195                 200                 205

Arg Tyr Arg Ala Val Ala Ser Trp Ser Arg Ile Lys Gly Ile Gly Val
    210                 215                 220

Pro Lys Trp Thr Ala Val Glu Ile Val Leu Ile Trp Val Val Ser Val
225                 230                 235                 240

Val Leu Ala Val Pro Glu Ala Ile Gly Phe Asp Ile Ile Thr Met Asp
                245                 250                 255

Tyr Lys Gly Ser Tyr Leu Arg Ile Cys Leu Leu His Pro Val Gln Lys
            260                 265                 270

Thr Ala Phe Met Gln Phe Tyr Lys Thr Ala Lys Asp Trp Trp Leu Phe
        275                 280                 285

Ser Phe Tyr Phe Cys Leu Pro Leu Ala Ile Thr Ala Phe Phe Tyr Thr
    290                 295                 300

Leu Met Thr Cys Glu Met Leu Arg Lys Lys Ser Gly Met Gln Ile Ala
305                 310                 315                 320

Leu Asn Asp His Leu Lys Gln Arg Arg Glu Val Ala Lys Thr Val Phe
                325                 330                 335

Cys Leu Val Leu Val Phe Ala Leu Cys Trp Leu Pro Leu His Leu Ser
            340                 345                 350

Arg Ile Leu Lys Leu Thr Leu Tyr Asn Gln Asn Asp Pro Asn Arg Cys
        355                 360                 365

Glu Leu Leu Ser Phe Leu Leu Val Leu Asp Tyr Ile Gly Ile Asn Met
    370                 375                 380

Ala Ser Leu Asn Ser Cys Ile Asn Pro Ile Ala Leu Tyr Leu Val Ser
385                 390                 395                 400
```

| Lys | Arg | Phe | Lys | Asn | Cys | Phe | Lys | Ser | Cys | Leu | Cys | Cys | Trp | Cys | Gln |
|---|---|---|---|---|---|---|---|---|---|---|---|---|---|---|---|
| | | | | 405 | | | | | 410 | | | | | 415 | |
| Ser | Phe | Glu | Glu | Lys | Gln | Ser | Leu | Glu | Glu | Lys | Gln | Ser | Cys | Leu | Lys |
| | | | 420 | | | | | 425 | | | | | 430 | | |
| Phe | Lys | Ala | Asn | Asp | His | Gly | Tyr | Asp | Asn | Phe | Arg | Ser | Ser | Asn | Lys |
| | | 435 | | | | | 440 | | | | | 445 | | | |
| Tyr | Ser | Ser | Ser | | | | | | | | | | | | |
| | 450 | | | | | | | | | | | | | | |

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CTTAAAATAC AATTCTATTT TTATCTTCAG 30

( 2 ) INFORMATION FOR SEQ ID NO:3:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

ACTAGTACTT TTTTTTTTTT TTTTTT 26

( 2 ) INFORMATION FOR SEQ ID NO:4:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

CAGCTTAAAA TACAATTCTA TTTTTATCTT 30

( 2 ) INFORMATION FOR SEQ ID NO:5:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

GGRARCCAGC ARAGRGCAAA 20

( 2 ) INFORMATION FOR SEQ ID NO:6:

( i ) SEQUENCE CHARACTERISTICS:
( A ) LENGTH: 31 base pairs
( B ) TYPE: nucleic acid
( C ) STRANDEDNESS: single (D) TOPOLOGY: linear (ii) MOLECULE TYPE: DNA (genomic)

(xi) SEQUENCE DESCRIPTION: SEQ ID NO:6:

ATACCCGGGA CCATGCAGCC GCCTCCAAGT C 31

(2) INFORMATION FOR SEQ ID NO:7:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

ATATCTAGAT CAAGATGAGC TGTATTTAT 29

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

AGGGTTTTCC CAGTCACGAC 20

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

GATAACAATT TCACACAGGA 20

(2) INFORMATION FOR SEQ ID NO:10:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Glu Glu Lys Gln Ser Cys Leu Lys Phe Lys Ala Asn Asp His Gly
1 5 10 15

(2) INFORMATION FOR SEQ ID NO:11:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Pro Arg Thr Ile Ser Pro Pro Pro Cys Gln Gly Pro Ile Glu Ile Cys
1 5 10 15

(2) INFORMATION FOR SEQ ID NO:12:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Asp Pro Asn Arg Cys Glu Leu Leu Ser Phe Leu Leu
1 5 10

(2) INFORMATION FOR SEQ ID NO:13:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:13:

Ser Leu Lys Tyr Asn Ser Ile Phe Ile Phe Cys
1 5 10

(2) INFORMATION FOR SEQ ID NO:14:

(i) SEQUENCE CHARACTERISTICS:
(A) LENGTH: 85 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

CTTTCTATTC TCACTCCGCT GAANNSNNSN NSNNSNNSNN SNNSNNSNNS NNSNNSNNSN 60

NSNNSNNSCC GCCTCCACCT CCACC 85

(2) INFORMATION FOR SEQ ID NO:15:

(i) SEQUENCE CHARACTERISTICS:
(A) LENGTH: 93 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: unsure
(B) LOCATION:
(C) OTHER INFORMATION: /note= "N is inosine"

(xi) SEQUENCE DESCRIPTION: SEQ ID NO:15:

GGCCGGTGGA GGTGGAGGCG GNNNNNNNNN NNNNNNNNNN NNNNNNNNNN NNNNNNNNNN 60

NNNNNNTTCA GCGGAGTGAG AATAGAAAGG TAC 93

(2) INFORMATION FOR SEQ ID NO:16:

(i) SEQUENCE CHARACTERISTICS:

( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GCTGCCCGAG AGATCTGTAT ATATGAGTAA ACTTGG 36

( 2 ) INFORMATION FOR SEQ ID NO:17:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

GCAGGCTCGG GAATTCGGGA AATGTGCGCG GAACCC 36

( 2 ) INFORMATION FOR SEQ ID NO:18:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

AAACTTCCTC ATGAAAAAGT C 21

( 2 ) INFORMATION FOR SEQ ID NO:19:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

AGAATAGAAA GGTACCACTA AAGGA 25

( 2 ) INFORMATION FOR SEQ ID NO:20:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

TCGAAAGCAA GCTGATAAAC CG 22

( 2 ) INFORMATION FOR SEQ ID NO:21:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

ACAGACAGCC CTCATAGTTA GCG 23

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

CTGTGCTGAG TCTATGTGCT 20

( 2 ) INFORMATION FOR SEQ ID NO:23:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

TACAATTCTA TTTTTATCTT CAGATATCGA GCTGTTGC 38

( 2 ) INFORMATION FOR SEQ ID NO:24:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

AAAAATAGAA TTGTATTTTA AGCTGTCAAT ACTCAGAGC 39

( 2 ) INFORMATION FOR SEQ ID NO:25:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

TTTAGTGGTA CCTTTCTATT CTCACTCGGC CGAAACTGT 39

( 2 ) INFORMATION FOR SEQ ID NO:26:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

AAAGCGCAGT CTCTGAATTT ACCG 24

-continued ( 2 ) INFORMATION FOR SEQ ID NO:27:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

```
Ala Glu Xaa Xaa Xaa Xaa Xaa Xaa Xaa Xaa Xaa Xaa Xaa Xaa Xaa Xaa
1               5                   10                  15

Xaa Pro Pro Pro Pro Pro Pro
            20
```

ENDOTHELIN $B_1$, ($ETB_1$) RECEPTOR POLYPEPTIDE AND ITS ENCODING NUCLEIC ACID METHODS, AND USES THEREOF

DESCRIPTION

1. Technical Field

This invention relates to the fields of molecular biology and pharmaceutical research. More specifically, this invention relates to the identification and recombinant expression of a new endothelin B receptor, named $ETB_1$, and its use to measure endothelin signal transduction and identification of new endothelin agonists and antagonists.

2. Background of the Invention

Endothelin-1 is a 21-amino acid peptide produced by vascular endothelial cells. Endothelin-2 and endothelin-3 are closely related peptides. Endothelins have a potent vasoconstrictive effect and a sustained, potent pressor effect, which are mediated by binding of endothelins to their receptors.

Increased endothelin levels are associated with cardiogenic shock, hypertension, pulmonary hypertension, acute myocardial infarction, uremia, Crohn's disease, ulcerative colitis, and are also observed following orthotopic liver transplantation and major abdominal surgical procedures. Endothelin may have a pathophysiologic role in sepsis, congestive heart failure, coronary spasm, cyclosporine nephrotoxicity, vasculitis, and pregnancy-associated toxemia.

Only two endothelin receptors are presently known, ETA and ETB. The cDNA sequence of the ETB $_1$ receptor is reported in Nakamuta et al.,*Biochem & Biophys Res Comm* 177(1): 34–39 (1991); Ogawa et al., *Biochem & Biophys Res Comm* 178(1): 248–255 (1991); and Sakamoto et al., *Biochem & Biophys Res Comm* 178(2): 656–663 (1991). The amino acid sequence of the ETA receptor is reported in Nakamuta et al., and Ogawa et al., supra. Study of their amino acid sequences shows that ETA and ETB are members of the seven transmembrane receptor family. This type of receptor contains seven helical domains which span the cell membrane. The seven transmembrane regions are linked by three intracellular and three extracellular loops; in addition, the receptor possesses an extracellular amino terminal tail and an intracellular carboxyl terminal tail.

The extra- and intracellular loops contribute to the endothelin binding and the signal transduction activity of the receptor. For example, the intracellular domains of the receptor are known to be coupled to guanyl-nucleotide-binding proteins, or G-proteins. G-proteins interconvert between GDP- and GTP-binding forms. Binding of endothelin to the receptor triggers the conversion of the G-protein to its GTP-binding form, which initiates the cascade of reactions to generate the desired biological response. This cascade is called signal transduction. Specifically, signal transduction of the endothelin receptors causes an increase of intracellular $Ca^{2+}$ levels and activation of phospholipase C. Signal transduction can be measured by observing the levels of inositol triphosphate ($IP_3$) and diacylglycerol (DAG), which are increased due to phospholise C activation and cyclic AMP (cAMP).

Though the role of the G-proteins has been elucidated, the intracellular loop interactions with these proteins and with other proteins are unknown.

DISCLOSURE OF THE INVENTION

Applicants have identified a new endothelin receptor, named endothelin $B_1$. receptor ($ETB_1$ receptor). This receptor contains a decapeptide insert in the second cytoplasmic loop which are not present in the known endothelin B receptor. The decapeptide insert is shown in bold in SEQ ID NO: 1, amino acid numbers 199 to 208.

The decapeptide insert is encoded by last 30 nucleotides of intron 2 of human ETB receptor gene. The gene thus provides a template for two different RNA splice variants. The ETB $_1$ receptor cDNA splice variant appears to be species specific. as shown by PCR studies and the bovine intron sequences reported in Mizuno et al., *Biochem J* 287: 305–309 (1992). Though, in Arai et al., *J Biol Chem* 268(5): 3463–3470 (1993), some human intron sequences have been reported for the ETB receptor gene, not all the possible splice sites have been identified. The putative splice sites were determined by the reported cDNA sequences. Applicants discovered that the $ETB_1$, mRNA is present in very low concentrations.

Thus, it is an object of the invention to provide native endothelin $B_1$ receptor substantially free of nucleic acids, for identifying new endothelin agonists and antagonists.

Another object of the invention is to provide endothelin $B_1$ receptor polypeptides that are mutants, fragments, and fusions of the newly identified endothelin $B_1$ receptor.

Yet another object of the invention is to provide polynucleotides that encode the mutants, fragments, and fusions, as well as the native endothelin $B_1$ receptor. These DNA molecules can be operably linked to heterologous promoters and origins of replication to construct expression vectors. The vectors can be introduced into suitable host cells for endothelin $B_1$ receptor polypeptides expression.

Another object of the invention is to provide a host cell containing a polynucleotide molecule encoding an endothelin $B_1$ receptor polypeptide operably linked to a heterologous promoter.

A further object of the invention is to provide a method for producing endothelin $B_1$ receptor polypeptides. The method comprises:

(a) providing a host cell comprising a vector having at least a promoter operably linked to a DNA molecule encoding an endothelin $B_1$ receptor polypeptide wherein said promoter is heterologous to said DNA molecule; and (b) culturing the host cell under conditions which induce expression of the endothelin $B_1$ receptor polypeptide.

Yet another object of the invention is to provide method for determining endothelin $B_1$ receptor signal transduction activity to identify endothelin agonists or antagonists. The method comprises:

(a) providing a cell expressing an endothelin $B_1$ receptor polypeptide;

(b) exposing the expressed endothelin B1 receptor polypeptide to a substrate; and (c) measuring endothelin B1 receptor signal transduction activity.

Another object of the invention is to provide a method for detecting endothelin $B_1$ receptor polynucleotides. The method comprises:

(a) providing a nucleic acid probe which hybridizes to SEQ ID NO: 2;

(b) hybridizing a sample of polynucleotides to said probe to form a duplex; and (c) detecting said duplexes.

MODES OF CARRYING OUT THE INVENTION

A. Definitions

As used herein, the term "endothelin $B_1$ receptor" refers to the polypeptides found in nature with substantial amino acid sequence identity to SEQ ID NO: 1 and containing the decapeptide, SLKYNSIFIF, at approximately amino acid position 199 to 208. The decapeptide insert distinguishes these endothelin $B_1$ receptors from known endothelin B receptors.

"Endothelin $B_1$ receptor polypeptides" include mutants, fragments, and fusions as well as the native endothelin $B_1$ receptor. "Mutants" of the native endothelin $B_1$ receptor are polypeptides having an amino acid sequence which retain at least 50% amino acid sequence identity with SEQ ID NO: 1; more typically, at least 60%; even more typically, at least 80%. Preferably mutants will retain at least 85% amino acid sequence identity with SEQ ID NO: 1; more preferably, at least 90%; even more preferably, at least 95%. These differences may be conservative amino acid substitutions or deletions in the amino acid sequence. "Fragments" possess the same amino acid sequence of the native endothelin $B_1$ receptor polypeptide except the fragments lack the amino and/or carboxyl terminal sequences of the native $ETB_1I$ receptor, "Fusions" are mutants, fragments, or the native $ETB_1$ receptor that also include amino and/or carboxyl terminal amino acid extensions. The number or type of the amino acid substitutions is not critical, nor is the length or number of the amino acid deletions, or amino acid extensions that are incorporated in the endothelin $B_1$ receptor polypeptides. However, all of these polypeptides will exhibit at least 20% of the native endothelin $B_1$ receptor signal transduction activity. More typically, the polypeptides exhibit at least 40%, even more typically the polypeptides exhibit at least 60% of the native endothelin B, receptor signal transduction activity. All these polypeptides will retain at least than 50% amino acid identity with SEQ ID NO: 1; more typically, at least 60%; even more typically, at least 80%. Preferably, these polypeptides will retain at least 85% amino acid sequence identity with SEQ ID NO: 1; more preferably, at least 90%; even more preferably, at least 95%.

"Signal transduction activity" occurs when binding of endothelin-1, 2, or 3, to the $ETB_1$ receptor triggers the desired biological response in a cell or cell extract. The biological response is the result of a cascade of biochemical reactions. Measurement of any one of these reactions can indicate that the desired biological response was triggered. For example, $ETB_1$ receptor is a G-coupled protein which, when proper signal transduction activity occurs, triggers an increase of intracellular $Ca^{2+}$, $lP_3$, and DAG levels. An assay for increased levels of free cytosolic $Ca^{2+}$ is described in Sakurai et al., EP 480 381, and Adachi et al., *FEBS Lett* 311(2): 179–183 (1992). Intracellular $lP_3$ concentrations can be measured according to Sakurai et al., EP 480 381 and Amersham's inositol 1,4,5-trisphosphate assay system (Arlington Heights, Ill., U.S.A.). These assays are effective for determining $ETB_1$ receptor signal transduction activity whether the receptor is normally expressed by the cell or expressed by a heterologous cell type by recombinant techniques. Proper signal transduction activity depend not only on receptor/ligand binding but also depend on the presence of the needed intracellular proteins. Thus, though a number of cells are capable, via recombinant techniques, of expressing $ETB_1$ receptor polypeptides, no biological response will be detected despite proper receptor/ligand binding if the host cell does not produce the needed intracellular proteins. Signal transduction activity can be detected in cells that are known to express the $ETB_1$ receptor in humans, such as heart, lung, brain, and placental cells. Heterologous host cells, COS and Chinese Hamster Ovary (CHO) cells, for instance, can the desired biological response if altered to produce the receptor by recombinant techniques.

A composition containing A is "substantially free of" B when at least 85% by weight of the total A+B in the composition is A. Preferably, A comprises at least about 90% by weight of the total of A+B in the composition, more preferably at least about 95% or even 99% by weight.

A "promoter" is a DNA sequence that initiates and regulates the transcription of a coding sequence when the promoter is operably linked to the coding sequence. A promoter is "heterologous" to the coding sequence when the promoter is not operably linked to the coding sequence in nature. A "native" promoter is operably linked to the coding sequence in nature.

An "origin of replication" is a DNA sequence that initiates and regulates replication of polynucleotides, such as an expression vector. The origin of replication behaves as an autonomous unit of polynucleotide replication within a cell, capable of replication under its own control. With certain origins of replication, an expression vector can be reproduced at a high copy number in the presence of the appropriate proteins within the cell. Examples of origins are the $2\mu$ and autonomously replicating sequences, which are effective in yeast; and the viral T-antigen, effective in COS-7 cells.

Host cells capable of producing $ETB_1$ receptor polypeptides are cultured "under conditions inducing expression." Such conditions allow transcription and translation of the DNA molecule encoding the $ETB_1$ receptor polypeptide. These conditions include cultivation temperature, oxygen concentration, media composition, pH, etc. For example, if the trp promoter is utilized in the expression vector, the media will lack tryptophan to trigger the promoter and induce expression. The exact conditions will vary from host cell to host cell and from expression vector to expression vector.

A nucleic acid probe is said to "hybridize" with SEQ ID NO:2 if the probe can form a duplex or double stranded complex, which is stable enough to be detected. Hybridization of the probe to a polynucleotide having the nucleic acid sequence of SEQ ID NO:2 depends on (1) the sequence of the nucleic acid probe and (2) the hybridization conditions. The sequence of the probe need not be exactly complementary. For example, a non-complementary nucleotide sequence may be attached to the 5' end of the probe, with the remainder of the probe sequence being complementary to SEQ ID NO:2. Alternatively, non-complementary bases or longer sequences can be interspersed into the probe, provided that the probe sequence has sufficient complementarity with SEQ ID NO: 2 to hybridize therewith and thereby form a duplex which can be detected. The exact length and sequence of the probe will depend on the hybridization conditions, such as temperature, salt condition and the like. For example, for diagnostic applications, depending on the complexity of the analyte sequence, the nucleic acid probe typically contains 15–25 or more nucleotides, although it may contain fewer nucleotides. Short primers generally require cooler temperatures to form sufficiently stable hybrid complexes with the template.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, altered antibodies, univalent antibodies, the Fab proteins, and single domain antibodies. Antibodies do not possess the signal transduction activity of $ETB_1$ receptor polypeptides.

B. General Method

This invention provides the amino acid and nucleotide sequence of the $ETB_1$ receptor. With these disclosed sequences, nucleic acid probe assays and expression cassettes and vectors for $ETB_1$ receptor polypeptides can be produced. The expression vectors can be transformed into host cells to produce $ETB_1$ receptor polypeptides. The purified polypeptides can be used to produce antibodies to distinguishes ETB receptors from $ETB_1$ receptor polypeptides. Also, the host cells or extracts can be utilized for biological assays to isolate endothelin agonists or antagonists.

Nucleic Acid $ETB_1$ Receptor Probe Assays

Expression of $ETB_1$ receptor mRNA is maximal in, but not limited to, brain and placental cells. In contrast, $ETB_1$ receptor mRNA is present in heart, lung, brain, and placental cells, but is absent in uterine poly($A^+$) RNA. This data suggests that the $ETB_1$ transcript is tissue specific. This variation of mRNA levels in different cell types can be exploited with nucleic acid probe assays to determine tissue types. For example, PCR, branched DNA probe assays, or blotting techniques utilizing nucleic acid probes substantially identical or complementary to SEQ ID NO:2 can determine the presence of $ETB_1$ cDNA or mRNA and the absence of ETB cDNA or mRNA.

For tissue typing, the nucleic acid probes will hybridize by the nucleotide sequence encoding the decapeptide insert of $ETB_1$ receptor, shown in SEQ ID NO:2 or the complement of SEQ ID NO:2. Though many different nucleotide sequences will encode the decapeptide insert, SEQ ID NO:2 is preferred because it is the actual sequence present in human cells. Because cDNA is complementary to mRNA, for cDNA detection, the nucleic acid probe will hybridize complement of SEQ ID NO:2. In contrast, for mRNA detection, the nucleic acid probe will hybridize to SEQ ID NO:2, itself. The nucleic acid probe sequences need not be identical to SEQ ID NO:2 or its complement. Some variation in the sequence and length can lead to increased assay sensitivity if the nucleic acid probe can form a duplex with target nucleotides, which can be detected. Also, the nucleic acid probe can include additional nucleotides which bind to $ETB_1$ receptor sequence flanking the decapeptide insert to stabilize the formed duplex. Or, additional non-$ETB_1$ receptor sequence may be helpful as a label to detect the formed duplex.

Probes of at least 20 nucleotides, more preferably at least 30 nucleotides are useful in the nucleic acid probe assays described below.

These probes may be produced by synthetic procedures, such as the triester method of Matteucci et al. (*J. Am. Chem. Soc.* (1981) 103:3185), or according to Urdea et al. *Proc. Natl. Acad. Sci.* USA 80: 7461 (1983), or using commercially available automated oligonucleotide synthesizers.

One example of a nucleotide hybridization assay is described in Urdea et al., PCT W092/02526 and Urdea et al., U.S. Pat. No. 5,124,246, herein incorporated by reference. The references describe an example of a sandwich nucleotide hybridization assay. The described assay utilizes a microtiter plate as a solid support and five sets of oligonucleotides to detect the target sequences. The five oligonucleotide sets are:

(1) plate binding oligonucleotides (oligonucleotide attached to the solid phase in Urdea et al.), (2) capture oligonucleotides ("capture probes" in Urdea et al.), (3) labeled probes ("amplifier probes" in Urdea et al.), (4) branched amplifier oligonucleotides ("multimer" in Urdea et al.), and (5) enzyme-linked oligonucleotides ("labeled oligonucleotide" in Urdea et al.).

A microtiter plate is coated with the plate binding oligonucleotides (1). These plate binding oligonucleotides contain a sequence that is complementary to a sequence on the capture oligonucleotides (2). The capture oligonucleotides also comprise a second sequence that can hybridize to the target nucleic acids. Via the plate binding and capture oligonucleotides, the target nucleic acids are immobilized to the microtiter plate and separated from unwanted and unbound nucleotides by simply washing the plate.

The target nucleic acids are detected via a labeled probe (3). For this specific assay, the labeled probe comprises a region complementary to the target nucleic acids and region (s) complementary to a region on the branched amplifier oligonucleotides (4). The branched amplifier oligonucleotide comprises multiple regions, which hybridize with a region on the enzyme-linked oligonucleotides (5). The enzyme-linked oligonucleotides cleave light producing molecules that can be detected with a luminometer.

Alternatively, the Polymerase Chain Reaction (PCR) is another well-known means for detecting small amounts of target nucleic acids. The assay is described in Mullis et al., *Meth. Enzymol.* 155: 335–350 (1987); U.S. Pat. No. 4,683,195; and U.S. Pat. No. 4,683,202, incorporated herein by reference. This method, unfortunately, cannot quantitate the amount of target nucleic acids. Two "primer" nucleotides hybridize with the target nucleic acids and are used to prime the reaction. The primers may be composed of sequence within or flanking the decapeptide insert or both. The primers need not hybridize to SEQ ID NO:2 or its complement. A thermostable polymerase creates copies of target nucleic acids from the primers using the original target nucleic acids as a template. After a large amount of target nucleic acids are generated by the polymerase, they can be detected by more traditional methods, such as Southern blots. When using the Southern blot method, the labelled probe will hybridize to SEQ ID NO:2 or its complement.

Finally, mRNA or cDNA can be detected by traditional blotting techniques described in Sambrook et al., "Molecular Cloning: A Laboratory Manual" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with radioactivity.

Expression of $ETB_1$ Receptor Polypeptides

Preferably, $ETB_1$ receptor polypeptides are produced by recombinantly engineered host cells. These host cells are constructed by the introduction of an expression vector composed of at least a promoter operably linked to an $ETB_1$ receptor polypeptide coding sequence.

Such coding sequences can be constructed by synthesizing the entire gene or by altering an existing $ETB_1$ receptor polypeptide coding sequence. $ETB_1$ receptor polypeptides can be divided into four general categories: mutants, fragments, fusions, and the native $ETB_1$ receptor polypeptides. The native $ETB_1$ receptor polypeptides are those that occur in nature. The amino acid sequence of such polypeptides may vary slightly, less than by 10 amino acids from SEQ ID NO: 1, but will retain the decapeptide insert, which distinguishes $ETB_1$ receptors from the known ETB receptor.

The native $ETB_1$ receptor polypeptide coding sequence can be selected based on the amino acid sequence shown in SEQ ID NO: 1. For example, synthetic genes can be made using codons preferred by the host cell to encode the desired polypeptide. (See Urdea et al., *Proc. Natl. Acad. Sci.* USA 80: 7461 (1983).) Alternatively, the desired native $ETB_1$ receptor polypeptide coding sequence can be cloned from nucleic acid libraries using probes based on the nucleic acid sequence shown in EP 480 381 or Arai et al., *J Biol Chem* 268(5): 3463–3470 (1993), for example. Techniques for producing and probing nucleic acid sequence libraries are described, for example, in Sambrook et al., "Molecular Cloning: A Laboratory Manual" (New York, Cold Spring Harbor Laboratory, 1989). Other recombinant techniques, such as site specific mutagenesis, PCR, enzymatic digestion and ligation, can also be used to construct the desired $ETB_1$ receptor polypeptide coding sequence.

The native $ETB_1$ receptor polypeptide coding sequence can be easily modified to create the other classes of $ETB_1$ receptor polypeptides. For example, mutants can be created by making conservative amino acid substitutions that maintain or enhance $ETB_1$ receptor polypeptide signal transduction activity. The following are examples of conservative substitutions: Gly←→Ala; Val←→Ile←→Leu; Asp←→Glu; Lys←→Arg; Asn←→Gin; and Phe←→Trp←→Tyr. A subset of mutants, called muteins, is a group of polypeptides with the non-disulfide bond participating cysteines substituted with a neutral amino acid, generally, with serines. These mutants may be stable over a broader temperature range than native $ETB_1$ receptor polypeptides. Mutants can also contain amino acid deletions or insertions compared to the native $ETB_1$ receptor polypeptides. Mutants may include substitutions, insertions, and deletions outside the decapeptide insert region of $ETB_1$ receptor. Mutants will retain at least 20% of the signal transduction activity of the native $ETB_1$ receptor polypeptides. The coding sequence of mutants can be constructed by in vitro mutagenesis of the native $ETB_1$ receptor polypeptide coding sequences.

Fragments differ from mutant or native $ETB_1$ receptor polypeptides by amino and/or carboxyl terminal amino acid deletions. The number of amino acids that are truncated is not critical as long as the $ETB_1$ receptor fragment retains at least 20% of the signal transduction activity of the native $ETB_1$ receptor polypeptide. The coding sequence of such fragments can be easily constructed by cleaving the unwanted nucleotides from the mutant or native $ETB_1$ receptor polypeptide coding sequences.

Fusions are fragment, mutant, or native $ETB_1$ receptor polypeptides with additional amino acids at either or both of the termini. The additional amino acid sequence is not necessarily homologous to sequence found in native $ETB_1$ receptor polypeptides. The fusions, just as all $ETB_1$ receptor polypeptides, retain at least 20% of the signal transduction activity of the native $ETB_1$ receptor polypeptides. Coding sequence of the fusions can be constructed by ligating synthetic polynucleotides encoding the additional amino acids to fragment, mutant, or native $ETB_1$ coding sequences. $ETB_1$ receptor signal transduction activity of the $ETB_1$ receptor polypeptides can be determined by the methods described infra.

At the minimum, an expression vector will contain a promoter which is operable in the host cell and operably linked to an $ETB_1$ receptor polypeptide coding sequence. Expression vectors may also include signal sequences, terminators, selectable markers, origins of replication, and sequences homologous to host cell sequences. These additional elements are optional but can be included to optimize expression.

A promoter is a DNA sequence upstream or 5' to the $ETB_1$ receptor polypeptide coding sequence to be expressed. The promoter will initiate and regulate expression of the coding sequence in the desired host cell. To initiate expression, promoter sequences bind RNA polymerase and initiate the downstream (3') transcription of a coding sequence (e.g. structural gene) into mRNA. A promoter may also have DNA sequences that regulate the rate of expression by enhancing or specifically inducing or repressing transcription. These sequences can overlap the sequences that initiate expression. Most host cell systems include regulatory sequences within the promoter sequences. For example, when a repressor protein binds to the lac operon, an *E. coli* regulatory promoter sequence, transcription of the downstream gene is inhibited. Another example is the yeast alcohol dehydrogenase promoter, which has an upstream activator sequence (UAS) that modulates expression in the absence of a readily available source of glucose. Additionally, some viral enhancers not only amplify but also regulate expression in mammalian cells. These enhancers can be incorporated into mammalian promoter sequences, and the promoter will become active only in the presence of an inducer, such as a hormone or enzyme substrate (Sassone-Corsi and Borelli (1986) *Trends Genet*. 2:215; Maniatis et al. (1987) *Science* 236:1237).

Functional non-natural promoters may also be used, for example, synthetic promoters based on a consensus sequence of different promoters. Also, effective promoters can contain a regulatory region linked with a heterologous expression initiation region. Examples of hybrid promoters are the *E. coli* lac operator linked to the *E. coli* tac transcription activation region; the yeast alcohol dehydrogenase (ADH) regulatory sequence linked to the yeast glyceraldehyde-3-phosphate-dehydrogenase (GAPDH) transcription activation region (U.S. Pat. Nos. 4,876,197 and 4,880,734, incorporated herein by reference); and the cytomegalovirus (CMV) enhancer linked to the SV40 (simian virus) promoter.

A $ETB_1$ receptor polypeptide coding sequence may also be linked in reading frame to a signal sequence. The signal sequence fragment typically encodes a peptide comprised of hydrophobic amino acids which directs the $ETB_1$ receptor polypeptide to the cell membrane. Preferably, there are processing sites encoded between the leader fragment and the gene or fragment thereof that can be cleaved either in vivo or in vitro. DNA encoding suitable signal sequences can be derived from genes for secreted endogenous host cell proteins, such as the yeast invertase gene (EP 12 873; JP 62,096,086), the A-factor gene (U.S. Pat. No. 4,588,684), interferon signal sequence (EP 60 057).

A preferred class of secretion leaders, for yeast expression, are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008, incorporated herein by reference; EP 324 274). Additional leaders employing an alpha-factor leader fragment that provides for secretion include hybrid alpha-factor leaders made with a presequence of a first yeast signal sequence, but a pro-region from a second yeast alpha-factor. (See e.g., PCT WO 89/02463.)

Typically, terminators are regulatory sequences, such as polyadenylation and transcription termination sequences, located 3' or downstream of the stop codon of the coding sequences. Usually, the terminator of native host cell proteins are operable when attached 3' of the $ETB_1$ receptor polypeptide coding sequences. Examples are the Saccharomyces cerevisiae alpha-factor terminator and the baculovirus terminator. Further, viral terminators are also operable in certain host cells; for instance, the SV40 terminator is functional in CHO cells.

For convenience, selectable markers, an origin of replication, and homologous host cells sequences may optionally be included in an expression vector. A selectable marker can be used to screen for host cells that potentially contain the expression vector. Such markers may render the host cell immune to drugs such as ampicillin, chloramphenicol, erythromycin, neomycin, and tetracycline. Also, markers may be biosynthetic genes, such as those in the histidine, tryptophan, and leucine pathways. Thus, when leucine is absent from the media, for example, only the cells with a biosynthetic gene in the leucine pathway will survive.

An origin of replication may be needed for the expression vector to replicate in the host cell. Certain origins of replication enable an expression vector to be reproduced at a high copy number in the presence of the appropriate proteins within the cell. Examples of origins are the $2\mu$ and autonomously replicating sequences, which are effective in yeast; and the viral T-antigen, effective in COS-7 cells.

Expression vectors may be integrated into the host cell genome or remain autonomous within the cell. Polynucleotide sequences homologous to sequences within the host cell genome may be needed to integrate the expression cassette. The homologous sequences do not always need to be linked to the expression vector to be effective. For example, expression vectors can integrate into the CHO genome via an unattached dihydrofolate reductase gene. In yeast, it is more advantageous if the homologous sequences flank the expression cassette. Particularly useful homologous yeast genome sequences are those disclosed in PCT W090/01800, and the HIS4 gene sequences, described in Genbank, accession no. J01331.

The choice of promoter, terminator, and other optional elements of an expression vector will also depend on the host cell chosen. The invention is not dependent on the host cell selected. Convenience and the level of protein expression will dictate the optimal host cell. A variety of hosts for expression are known in the art and available from the American Type Culture Collection (ATCC). Bacterial hosts suitable for expressing an $ETB_1$ receptor polypeptide include, without limitation: Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. Immortalized mammalian host cells include but are not limited to CHO cells, HeLa cells, baby hamster kidney (BHK) cells, monkey kidney cells (COS), human hepatocellular carcinoma cells (e.g., Hep G2), and other cell lines. A number of insect cell hosts are also available for expression of heterologous proteins: *Aedes aegypti, Bombyx mori, Drosophila melanogaster*, and *Spodoptera frugiperda* (PCT WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Transformation

After vector construction, the desired $ETB_1$ receptor polypeptide expression vector is inserted into the host cell. Many transformation techniques exist for inserting expression vectors into bacterial, yeast, insect, and mammalian cells. The transformation procedure to introduce the expression vector depends upon the host to be transformed.

Methods of introducing exogenous DNA into bacterial hosts are well-known in the art, and typically protocol includes either treating the bacteria with $CaCl_2$ or other agents, such as divalent cations and DMSO. DNA can also be introduced into bacterial cells by electroporation or viral infection. Transformation procedures usually vary with the bacterial species to be transformed. See e.g., (Masson et al. (1989) *FEMS Microbiol. Lett.* 60:273; Palva et al. (1982) *Proc. NatI. Acad. Sci. USA* 79:5582; EP Publ. Nos. 036 259 and 063 953; PCT WO 84/04541, Bacillus), (Miller et al. (1988) *Proc. Nat. Acad. Sci.* 85:856; Wang et al. (1990) *J. Bacteriol.* 172:949, Campylobacter), (Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids in *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; Escherichia), (Chassy et al. (1987) *FEMS Microbiol. Lett.* 44:173 Lactobacillus); (Fiedler et al. (1988) *Anal. Biochem* 170:38, Pseudomonas); (Augustin et al. (1990) *FEMS Microbiol. Lett.* 66:203, Staphylococcus), (Barany et al. (1980) *J. Bacteriol.* 144:698; Harlander (1987) "Transformation of *Streptococcus lactis* by electroporation," in *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, Streptococcus).

Transformation methods for yeast hosts are well-known in the art, and typically include either the transformation of spheroplasts or of intact yeast cells treated with alkali cations. Electroporation is another means for transforming yeast hosts. See for example, *Methods in Enzymology*, Volume 194, 1991, "Guide to Yeast Genetics and Molecular Biology." Transformation procedures usually vary with the yeast species to be transformed. See e.g., (Kurtz et al. (1986) *Mol. Cell. Biol.* 6:142; Kunze et al. (1985) *J. Basic Microbiol.* 25:141; Candida); (Gleeson et al. (1986) *J. Gen. Microbiol.* 132:3459; Roggenkamp et al. (1986) *Mol. Gen. Genet.* 202:302; Hansenula); (Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces); (Cregg et al. (1985) *Mol. Cell. Biol.* 5:3376; Kunze et al. (1985) *J. Basic Microbiol.* 25:141; U.S. Pat. Nos. 4,837,148 and 4,929,555; Pichia); (Hinnen et al. (I1978) *Proc. Natl. Acad. Sci. USA* 75; 1929; Ito et al. (1983) *J. Bacteriol.* 153:163 Saccharomyces); (Beach and Nurse (1981) *Nature* 300:706; Schizosaccharomyces); (Davidow et al. (1985) *Curr. Genet.* 10:39; Gaillardin et al. (1985) *Curr. Genet.* 10:49; Yarrowia).

Methods for introducing heterologous polynucleotides into mammalian cells are known in the art and include viral infection, dextran-mediated transfection, calcium phosphate precipitation, polybrene mediated transfection, protoplast fusion, electroporation, encapsulation of the polynucleotide (s) in liposomes, and direct microinjection of the DNA into nuclei.

The method for construction of an expression vector for transformation of insect cells for expression of recombinant herein is slightly different than that generally applicable to the construction of a bacterial expression vector, a yeast expression vector, or a mammalian expression vector. In an embodiment of the present invention, a baculovirus vector is constructed in accordance with techniques that are known in the art, for example, as described in Kitts et al., *BioTechniques* 14: 810–817 (1993), Smith et al., *Mol. Cell. Biol.* 3: 2156 (1983), and Luckow and Summer, *Virol.* 17: 31 (1989). In one embodiment of the present invention, a baculovirus expression vector is constructed substantially in accordance to Summers and Smith, Texas Agricultural Experiment Station Bulletin No. 1555 (1987). Moreover, materials and methods for baculovirus/insect cell expression systems are commercially available in kit form, for example, the MaxBac® kit from Invitrogen (San Diego, Calif.).

Also, methods for introducing heterologous DNA into an insect host cell are known in the art. For example, an insect cell can be infected with a virus containing an $ETB_1$ receptor polypeptide coding sequence. When the virus is replicating in the infected cell, the $ETB_1$ receptor polypeptide will be expressed if operably linked to a suitable promoter. A variety of suitable insect cells and viruses are known and include following without limitation.

Insect cells from any order of the Class Insecta can be grown in the media of this invention. The orders Diptera and Lepidoptera are preferred. Example of insect species are listed in Weiss et al., "Cell Culture Methods for Large-Scale Propagation of Baculoviruses," in Granados et al. (eds.), *The Biology of Baculoviruses*: Vol. II *Practical Application for Insect Control*, pp. 63–87 at p. 64 (1987). Insect cell lines derived from the following insects are exemplary: *Carpocapsa pomeonella* (preferably, cell line CP-128); *Trichoplusia ni* (preferably, cell line TN-368); *Autograph californica; Spodoptera frugiperda* (preferably, cell line Sf9); *Lymantria dispar; Mamestra brassicae; Aedes albopictus; Orgyia pseudotsugata; Neodiprio sertifer; Aedes aegypti; Antheraea eucalypti; Gnorimoschema operceullela; Galleria mellonella; Spodoptera littolaris; Blatella germanic; Drosophila melanogaster; Heliothis zea; Spodoptera exigua; Rachiplusia ou; Plodia interpunctella; Amsaeta moorei; Agrotis c-nigrum, Adoxophyes orana; Agrotis segetum; Bombyx mori; Hyponomeuta malinellu;, Colias eurytheme; Anticarsia germmetalia; Apanteles melanoscelu; Arctia caja*; and *Porthetria dispar*. Preferred insect cell lines are from *Spodoptera frugiperda*, and especially preferred is cell line Sf9. The Sf9 cell line used in the examples herein was obtained from Max D. Summers (Texas A & M University, College Station, Texas, 77843, U.S.A.) Other *S. frugiperda* cell lines, such as IPL-Sf-21AE III, are described in Vaughn et al., In Vitro 13: 213–217 (1977).

The insect cell lines of this invention are suitable for the reproduction of numerous insect-pathogenic viruses such as parvoviruses, pox viruses, baculoviruses and rhabdcoviruses, of which nucleopolyhedrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Gallerai spp., and Lymantria spp. More prefferred are baculovirus strain *Autographa californica* NPV (AcNPV), *Rachiplusia ou* NPV, *Galleria mellonella* NPV, and any plaque purified strains of AcNPV, such as E2, R9, S1, M3, characterized and described by Smith et al., *J Virol* 30: 828–838 (1979); Smith et al., J Virol 33: 311–319 (1980); and Smith et al., *Virol* 89: 517–527 (1978).

Typically, insect cells *Spodoptera frugiperda* type 9 (SF9) are infected with baculovirus strain *Autographa californica* NPV (AcNPV) containing an $ETB_1$ receptor polypeptide coding sequence. Such a baculovirus is produced by homologous recombination between a transfer vector containing the coding sequence and baculovirus sequences and a genomic baculovirus DNA. Preferably, the genomic baculovirus DNA is linearized and contains a disfunctional essential gene. The transfer vector, preferably, contains the nucleotide sequences needed to restore the disfunctional gene and a baculovirus polyhedrin promoter and terminator operably linked to the $ETB_1$ receptor polypeptide coding sequence. (See Kitts et al., BioTechniques 14(5): 810–817 (1993).

The transfer vector and linearized baculovirus genome are transfected into SF9 insect cells, and the resulting viruses probably containing the desired coding sequence. Without a functional essential gene the baculovirus genome cannot produce a viable virus. Thus, the viable viruses from the transfection most likely contain the $ETB_1$ receptor polypeptide coding sequence and the needed essential gene sequences from the transfer vector. Further, lack of occlusion bodies in the infected cells are another verification that the $ETB_1$ receptor polypeptide coding sequence was incorporated into the baculovirus genome.

The essential gene and the polyhedrin gene flank each other in the baculovirus genome. The coding sequence in the transfer vector is flanked at its 5' with the essential gene sequences and the polyhedrin promoter and at its 3' with the polyhedrin terminator. Thus, when the desired recombination event occurs the $ETB_1$ receptor polypeptide coding sequence displaces the baculovirus polyhedrin gene. Such baculoviruses without a polyhedrin gene will not produce occlusion bodies in the infected cells. Of course, another means for determining if coding sequence was incorporated into the baculovirus genome is to sequence the recombinant baculovirus genomic DNA. Alternatively, expression of the desired $ETB_1$ receptor polypeptide by cells infected with the recombinant baculovirus is another verification means.

Monitoring $ETB_1$ Receptor Polypeptide Expression Levels

Immunoassays and ligand binding assays can be utilized to determine if the transformed host cell is expressing the desired $ETB_1$ receptor polypeptide.

For example, an immunofluorescence assay can be easily performed on transformed host cells without separating the $ETB_1$ receptor polypeptides from the cell membrane. The host cells are first fixed onto a solid support, such as a microscope slide or microtiter well. This fixing step permeabilizes the cell membrane. Next, the fixed host cells are exposed to an anti-$ETB_1$ receptor polypeptide antibody. Preferably, to increase the sensitivity of the assay, the fixed cells are exposed to a second antibody, which is labelled and binds to the anti-$ETB_1$ receptor polypeptide antibody. Typically, the secondary antibody is labelled with an fluorescent marker. The host cells which express the $ETB_1$ receptor polypeptides will be fluorescently labelled and easily visualized under the microscope. See, for example, Hashido et al., *Biochem & Biophys Res Comm* 187(3): 1241–1248 (1992).

Also, the $ETB_1$ receptor polypeptides do not need to be separated from the cell membrane for ligand binding assay. The host cells may be fixed to a solid support, such as a microtiter plate. Alternatively, a crude membrane fraction can be separated from lysed host cells by centrifugation (See Adachi et al., *FEBS Lett* 311(2): 179–183 (1992)). The fixed host cells or the crude membrane fraction is exposed to labelled endothelin, or other suitable ligand such as an endothelin agonist or antagonist. Typically, the endothelin is labelled with radioactive atoms. The host cells which express the desired $ETB_1$ receptor polypeptide will bind with the labelled ligand which can be easily detected.

Purification

The purified $ETB_1$ receptor polypeptides are useful for signal transduction assays, ligand/receptor binding assays. The purified polypeptides can also be utilized to produce $ETB_1$ receptor polypeptide specific antibodies.

For ligand/receptor binding studies, the crude cell membrane fractions can be utilized. These membrane extracts can be isolated from cells which expressed $ETB_1$ receptor polypeptides by lysing the cells and separating the cell membrane fraction from the intracellular fractions by centrifugation. See Adachi et al., *FEBS Lett* 311 (2): 179–183 (1992) for an endothelin binding assay procedure using cell membranes. Alternatively, whole cells, expressing $ETB_1$ receptor polypeptides, can be cultured in a microtiter plate, for example, and used for endothelin binding assay. See Sakamoto et al., *Biochem & Biophys Res Comm* 178(2): 656–663 (1991) for a description of such an assay.

Once the polypeptide has been dissociated from the cell membrane, the desired $ETB_1$ receptor polypeptide can also be affinity purified with specific $ETB_1$ antibodies.

Antibodies

Antibodies against $ETB_1$ receptor polypeptides are useful for affinity chromatography, immunofluorescent assays, and distinguishing ETB from $ETB_1$ receptor polypeptides. Antibodies which recognize the decapeptide insert are of particular interest.

Such antibodies can be used to distinguish $ETB_1$ receptor polypeptides from ETB receptors. These antibodies are useful in immunofluorescent assays when the cells are processed so that the membrane is made permeable. The permeablization of the cell membrane permits the antibodies to bind to the decapeptide insert of the second cytoplasmic loop of the $ETB_1$ receptor polypeptides. Peptides containing the decapeptide insert, SLKYNSIFIF, can be easily synthesized using known automated synthesizer and gel purified for antibody production.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50–200 $\mu$g/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating at 4° C. for 2–18 hours. The serum is recovered by centrifugation (e.g., 1,000 ×g for 10 minutes). About 20–50 ml per bleed may be obtained from rabbits.

Monoclonal antibodies are prepared using the method of Kohler and Milstein, *Nature* (1975) 256:495–96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3', 5,5'-tetramethylbenzidine (TNB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Use in Biological Assays $ETB_1$ receptor polypeptides can also be used to screen peptide libraries to determine the amino acid sequence of endothelin peptide agonist or antagonists.

A "library" of peptides may be synthesized following the methods disclosed in U.S. Pat. No. 5,010,175, and in PCT W091/17823, both incorporated herein by reference in full. Briefly, one prepares a mixture of peptides, which is then screened to determine the peptides exhibiting the desired signal transduction and receptor binding activity. In the '175 method, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected $ETB_1$ receptor polypeptide. The peptides are then tested for their ability to inhibit or enhance $ETB_1$ receptor signal transduction activity. Peptides exhibiting the desired activity are then isolated and sequenced.

The method described in '17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to the desired $ETB_1$ receptor polypeptide. Each subpool that produces a positive result is then resynthesized as a group of smaller subpools (sub-subpools) containing, e.g., 20–100 candidates, and reassayed. Positive sub-subpools may be resynthesized as individual compounds, and assayed finally to determine the peptides, which exhibit a high binding constant. Then, these peptides can be tested for their ability to inhibit or enhance the $ETB_1$ signal transduction activity. The methods described in '17823 and U.S. Pat. No. 5,194,392 (herein incorporated by reference) enable the preparation of such pools and subpools by automated techniques in parallel, such that all synthesis and resynthesis may be performed in a matter of days.

Endothelin peptide agonists or antagonists are screened using any available method. The methods described herein are presently preferred. The assay conditions ideally should resemble the conditions under which the $ETB_1$ receptor signal transduction is exhibited in vivo, i.e., under physiologic pH, temperature, ionic strength, etc. Suitable agonists or antagonists will exhibit strong inhibition or enhancement of the $ETB_1$, signal transduction activity at concentrations which do not raise toxic side effects in the subject. Agonists or antagonists which compete for binding to the $ETB_1$ receptor ligand binding site may require concentrations equal to or greater than the $ETB_1$ receptor concentration, while inhibitors capable of binding irreversibly to the $ETB_1$ receptor may be added in concentrations on the order of the $ETB_1$ receptor concentration.

Signal Transduction Assays

Most cellular $Ca^{2+}$ ions are sequestered in the mitochondria, endoplasmic reticulum, and other cytoplasmic vesicles, but binding of endothelin to $ETB_1$ will trigger the increase of free $Ca^{2+}$ ions in the cytoplasm. With fluorescent dyes, such as fura-2, the concentration of free $Ca^{2+}$ can be monitored. The ester of fura-2 is added to the media of the host cells expressing $ETB_1$ receptor polypeptides. The ester of fura-2 is lipophilic and diffuses across the membrane. Once inside the cell, the fura-2 ester is hydrolyzed by cytosolic esterases to its non-lipophilic form, and then the dye cannot diffuse back out of the cell. The non-lipophilic form of fura-2 will fluoresce when it binds to the free $Ca^{2+}$ ions, which are released after binding of a ligand to the $ETB_1$ receptor. The fluorescence can be measured without lysing the cells at an excitation spectrum of 340 nm or 380 nm and at fluorescence spectrum of 500 nm. See Sakurai et al., EP 480 381 and Adachi et al., *FEBS Lett* 311(2): 179–183 (1992) for examples of assays measuring free intracellular $Ca^{2+}$ concentrations.

The rise of free cytosolic $Ca^{2+}$ concentrations is preceded by the hydrolysis of phosphatidylinositol 4,5-bisphosphate. Hydrolysis of this phospholipid by the plasmamembrane enzyme phospholipase C yields 1,2-diacylglycerol (DAG), which remains in the membrane, and the water-soluble inosital 1,4,5-trisphosphate ($IP_3$). Binding of endothelin or endothelin agonists will increase the concentration of DAG and $IP_3$. Thus, signal transduction activity can be measured by monitoring the concentration of these hydrolysis products.

To measure the $IP_3$ concentrations, radioactively labelled $^3H$-inositol is added to the media of host cells expressing $ETB_1$ receptor polypeptides. The $^3H$-inositol taken up by the cells and after stimulation of the cells with endothelin or endothelin agonist, the resulting inositol triphosphate is separated from the mono and di-phosphate forms and measured. See Sakurai et al., EP 480 381. Alternatively, Amersham provides an inosital 1,4,5-trisphosphate assay system. With this system Amersham provides tritylated inosital 1,4,5-trisphosphate and a receptor capable of distinguishing the radioactive inositol from other inositol phosphates. With these reagents an effective and accurate competition assay can be performed to determine the inositol triphosphate levels.

C. EXAMPLES

The examples presented below are provided as a further guide to the practitioner of ordinary skill in the art, and are not to be construed as limiting the invention in any way.

EXAMPLE 1

Tissue Typing by PCR Utilizing $ETB_1$ Insert Specific Primers

Tissue distribution of the mRNA encoding the native $ETB_1$ receptor was performed by reverse transcriptase PCR.

A. RNA Isolation from Tissue

Approximately 0.1 g of tissue is minced in ice or homogenized at room temperature with 1 ml of denaturing solution (4M guanidinium thiocyanate; 25 mM sodium citrate, pH 7.0; 0.5% (wt/v) sarcosyl; 0.1M beta mercaptoethanol). Sequentially, 0.1 ml of 2M sodium acetate, pH 4.0 is added, then 1 ml phenol, and finally 0.2 ml chloroform/isoamyl alcohol (49:1) are added to the homogenate, and the sample is cooled on ice for 15 minutes. Samples are centrifuged at 10,000 g for twenty minutes at 4° C. The aqueous phase, containing the RNA, is removed from the pellet. Next, the aqueous phase is mixed with 1.0 ml isopropanol and incubated at −20° C. for one hour to precipitate the RNA. The RNA is pelleted from the sample by centrifugation at 10,000 g for 20 minutes, and the resulting pellet was dissolved in 0.3 ml of denaturing solution. The redissolved pellet is transferred into a 1.5 ml Eppendorf tube, and the RNA is precipitated with one volume of isopropanol and incubated at −20° C. for one hour. After centrifugation in an Eppendorf centrifuge for ten minutes at 4° C., the aqueous phase is removed, and the RNA pellet is washed in 75% (v/v) ethanol. The RNA pellet is dissolved in 50 $\mu$l TE (10 mM Tris, pH 7.0 and 1 mM EDTA).

B. Generating cDNA by Reverse Transcriptase Polymerase Chain Reaction (RTPCR) from RNA cDNA can be synthesized from RNA isolated from the desired tissue, or RNA from human tissues can be purchased from Clontech, Palo Alto, Calif., U.S.A.

cDNA was synthesized from 5 $\mu$g of human brain poly (A+) RNA, from Clontech, Palo Alto, Calif., U.S.A., using a 3' RACE (Rapid Amplification of cDNA Ends) kit from Life Technologies, Gaithersburg, Md., U.S.A. This procedure was designed to convert up to 1 μg of total RNA into first strand cDNA. Although poly(A)$^+$RNA can be used in this protocol, this level of purity is typically not necessary. A control RNA was included in the kit to aid in verification of that the reaction performs correctly. To use the control RNA as a template for the cDNA synthesis, 2 μl of the control RNA (100 ng) can be substituted in the cDNA reaction in place of the sample RNA. (Note: Each component was mixed and quickly centrifuged before each use.)

Five μg of total or poly (A)$^+$selected RNA was added to 13 μl of DEPC-treated water to a 0.5 ml microcentrifuge tube. Next, 1 μl of the 10 μM solution containing primer Vet119 was added to the tube and mixed gently. The sequence, 5' to 3' of Vet119 is AC TAG TAC TTT TTT TTT TTT TTT TTT (SEQ ID NO:3). The mixture was heated to 65° C. for 10 minutes and chilled for two minutes on ice. The contents of the tube were centrifuged and the following was added:

10 X synthesis buffer . . . 2 μl 10 mM dNTP mix . . . 1 μl 0.1 M DTT . . . 2 μl

The final composition of the mixture was 20 mM Tris-HC1 (pH 8.4);

50 mM KCl;

2.5 mM $MgCl_2$;

100 μg/ml bovine serum albumin (BSA);

10 mM DTT;

500 nM Vet 119;

500 μM each of dATP, dCTP, dGTP, dTTP; and

≦1 μg (<50 ng/μl) of RNA.

The mixture was mixed gently and spun down by brief centrifugation. The mixture was equilibrated to 42° C. for 2 minutes. Next, 1 μl of SUPERSCRIPT RT was added. The mixture was then incubated in a 42° C. water bath or heat block for 30 minutes. The mixture was briefly centrifuged to collect the liquid at the bottom of the tube. The mixture was then placed on ice and 1 μl of RNase H was added to the tube and mixed. The mixture was incubated at 42° C. for 10 minutes.

The resulting cDNA was purified by adsorption to GLASSMAX filters from Life Technologies, Gaithersburg, Md., U.S.A. Ninety five μl of binding buffer was added to the cDNA reaction mixture. The entire mixture was transferred to a GLASSMAX Spin Cartridge. The cartridge was centrifuged at 13,000 g for 20 seconds. The flowthrough material was retained in a separate tube. Next, the cartridge was washed with 400 μl of cold 1X wash buffer, and the cartridge was centrifuged at 13,000 g for 20 seconds, and the flowthrough material was discarded. This wash step was repeated two more times. Finally, the cartridge was washed with 400 μl of cold 70% ethanol. The cartridge was centrifuged at 13,000 g for 20 seconds, and the flowthrough material was discarded. Next, the cartridge was centrifuged for 1 minute at 13,000 g; then, the cartridge was inserted into a new collection tube, and 50 μl distilled water at 65° C. was added. The cartridge was centrifuged at 13,000 g for 20 seconds. The flowthrough material contained the cDNA material for amplification.

C. Tissue Typing by PCR

Two μl of the eluted material was used as a template for PCR. One pmole of each primer and 1 unit of polymerase from Perkin Elmer, Norwalk, Conn., U.S.A., were added to a final volume of 50 μl, and included 2.5 μl formamide, 10 mM-Tris/HCI (pH 8.3), 50 mM-KCl, 3.5 mM-$MgCl_2$, and 0.2 mM dNTPs. Amplification was accomplished by performing PCR for 40 cycles at 94° C. for 1 minute, 50° C. for 1 minute, and 72° C. for 2 minutes. Five μl of the product were electrophoresed to visualize PCR products. All PCR products were cloned using the TA cloning kit (from Invitrogen, San Diego, Calif., U.S.A.) and sequenced by cycle sequencing using an Applied Biosystems sequencer according to established techniques. All sequences were confirmed by sequencing both strands.

Oligo dT primed cDNA was amplified with insert specific primer Vet71, SEQ ID NO:4, and ETB specific primer Vet85, SEQ ID NO:5 The sequence of the primers was as follows:

Vet71: 5' CAG CTT AAA ATA CAA TTC TAT TTT TAT CTT 3'

Vet85: 5' GGR ARC CAG CAR AGR GCA AA 3'.

PCR products were obtained with human brain, heart, lung, and placenta, but no PCR products were obtained from uterus poly(A+) RNA. In a control reaction with ETB specific primers, Vet100, SEQ ID NO:22, and Vet85, SEQ ID NO:4, all samples yielded PCR products. The sequence of Vet100 was 5' CTG TGC TGA GTC TAT GTG CT 3'.

EXAMPLE 2

Construction of a $ETB_1$ Coding Sequence

The coding sequence for ETB receptor was isolated from poly(A)$^+$ RNA. DNA encoding the decapeptide sequence of SEQ ID NO:2 was incorporated by overlap PCR. The final $ETB_1$, coding sequence encodes the amino acid sequence of SEQ ID NO: 1. The coding sequence contains XmaI and XbaI ends for cloning convenience.

The coding sequence was constructed from the cDNA of the ETB coding sequence synthesized from isolated poly (A$^+$) RNA from human brain. cDNA was synthesized from the RNA according to Example 1, section B. The RNA was purchased from Clontech, Palo Alto, Calif., U.S.A.

The ETB receptor polypeptide cDNA was isolated from the poly(A$^+$) RNA by PCR. Two μl of the RNA was used as template for the reaction with the following reagents: 1 pmole of primers Vet126 (SEQ ID NO:6) and Vetl27 (SEQ ID NO:7), 1 unit of polymerase from Perkin Elmer, Norwalk, Conn., U.S.A., 2.5 μl formamide, 10 mM-Tris/HCI (pH 8.3), 50 mM-KCI, 3.5 mM-$MgCl_2$, 0.2 mM dNTPs and water was added to a final volume of 50 μl. The PCR product was cloned into PCR-II vector from Invitrogen, San Diego, Calif., U.S.A. The sequence of the primers,(SEQ ID NO:5) and (SEQ ID NO:) was as follows:

Vetl26: 5' ATA CCC GGG ACC ATG CAG CCG CCT CCA AGT C 3'

Vetl27: 5' ATA TCT AGA TCA AGA TGA GCT GTA TTT AT 3'

The native $ETB_1$ receptor polypeptide coding sequence was constructed by overlap PCR according to Shyamala et al., *Gene* 97: 1–6 (1991). This PCR technique permits the incorporation of mutations within a desired DNA fragment, such as a complete coding sequence. The desired DNA fragment is first synthesized in two double stranded parts. The DNA sequence of the first part is the 5' end of the desired fragment to the mutagenesis site, and the DNA sequence second part contains the remainder of the desired DNA fragment from the site of mutagenesis to the 3' end. These parts are constructed using PCR with the mutation incorporated into the PCR primers. Thus, two sets of primers are utilized.

The desired primers are kinased, so that the PCR products which result from the elongation of these primers can be preferentially digested by an exonuclease. The result of this digestion is two single stranded products that overlap and can hybridize at the mutatgenesis site. Together, the single stranded products span the entire sequence of the desired fragment. Then PCR is used to create a complete double stranded DNA fragment. This technique was used to incorporate the decapeptide insert into the native ETB receptor polypeptide coding sequence.

Primers Vet 122, SEQ ID NO:23 and Vet 123, SEQ ID NO:24, were kinased as described below. The sequence of the primers was as follows:

Vet122: 5' TAC AAT TCT ATT TTT ATC TTC AGA TAT CGA GCT GTT GC 3'

Vet123: 5' AAA AAT AGA ATT GTA TTT TAA GCT GTC AAT ACT CAG AGC 3'

The primers were added to a solution whose final volume was 13 μl. The solution consisted of 1 μl of 0.2 M ATP, 10 μl of 50 μM primers, 1.3 μl of 10X kinasing buffer, and 1 μl polynucleotide kinase from New England Biolabs, Boston, Mass., U.S.A.,. The solution was incubated at 37° C. for 15 minutes.

Two μl of PCR-II vector with the native $ETB_1$ receptor polypeptide coding sequence was used as a template for the PCR. Two PCR reactions containing the following reagents were performed sequentially: 2.5 μl formamide, 10 mM Tris/HCI (pH 8.3), 50 mM KCl, 3.5 mM $MgCI_2$, 0.2 mM dNTPs, as described in section B, and 1 pmole of each of the desired primers, the final reaction volume was 50 μl. One reaction was with Vet 122 and M13 forward primers, and the second reaction was with Vet 123 and M13 reverse primers. The sequence of the M13 forward and reverse primers were as follows:

M13 Forward: 5' AGG GTT TTC CCA GTC ACG AC 3' (SEQ ID NO:8)

M13 Reverse: 5' GAT AAC AAT TTC ACA CAG GA 3' (SEQ ID NO:9)

Thirty repetitions of the following temperature cycle was used: 94° C. for 1 minute, 50° C. for 1 minute, and 72° C. for 2 minutes.

Next, the double stranded products were digested with λ exonuclease to produce the desired single stranded products. After both PCR reactions, 5 μl of 67 mM glycine, titrated to pH 9.4 with NaOH, was added to 40 μl of the final amplification reaction. Then, 5 units of λ exonuclease (BRL, Gaithersburg, Md., U.S.A.) was added to the solution and incubated at 37° C. for 30 minutes. The digest DNA was passed through a Sephacryl S-300 spin column.

To facilitate overlap hybridization, 15 μl of the pass through from the two reaction were mixed with the amplification reagents as described above and extended with the addition of Klenow at each cycle for 5 temperature cycles of 94° C. for 1 minute denaturation; and 37° C. for 1 minute extension. After hybridization, PCR techniques were used to create the desired double stranded $ETB_1$ receptor polypeptide coding sequence. One unit of Taq polymerase was added to the solution containing the hybridized fragments, and the solution was subjected to 20 temperature cycles of 94° C. for 1 minute, 50° C. for 1 minute, and 72° C. for 2 minutes. The amplified DNA was digested with XmaI and XbaI and cloned into BacPak9 and pCMV vectors.

EXAMPLE 3

Construction of a Mammalian Cell $ETB_1$ Receptor Polypeptide Expression Vector The resulting XmaI/XbaI $ETB_1$ receptor polypeptide fragment was ligated with a XmaI/XbaI fragment pCMV9D, a mammalian expression vector. pCMV9D contains the cytomegalovirs immediate early 1 enhancer/promoter, a poly A sequence terminator, the simian virus 40 origin of replication, the ampicillin resistance gene, and mouse dihydrofolate reductase (DHFR) gene under the control of the adenovirus promoter. pCMV9D is a derivative of the pCMV6a expression vector, which has been altered to include the DHFR selectable marker.

Plasmid pCMV6a is a mammalian cell expression vector which contains the transcriptional regulatory region from human cytomegalovirus major immediate early region (HCMV IE1) of the Towne strain. The plasmid contains the SV40 polyadenylation region derived from pSV7d (described in U.S. Pat. No. 5,156,949) as a 700 bp PvuI-SalI fragment; the SV40 origin of replication derived from pSVT2 (Meyers et al., *Cell* 25: 373–384 (1981); Rio et al., *Cell* 32: 1227–1240 (1983)) as a 1.4 kb PvuI-EcoRl (the ends were filled in with Klenow); and the HCMV IEI promoter as a 1.7 kb SspI-SalI fragment derived from a subclone of the human cytomegalovirus (Towne Strain). The HCMV IE1 promoter region contains the region encoding the first exon (5' untranslated), the first intron and the start of the second exon (where the SalI site was created by in vitro mutagenesis). This intron is included on the assumption that spliced transcripts lead to faster processing and more stable mRNA. The expression vector also has an SV40 origin of replication to permit transient expression in COS7 cells, and a bacterial β-lactamase gene to permit DNA cloning by selection for ampicillin resistance.

The DHFR selectable marker was isolated from pAd-DHFR. This vector includes the adenovirus-2 major late promoter (Ad-MLP, map units 16–27.3) fused to the 5' untranslated sequences of the mouse DHFR cDNA (Nunberg et al., *Cell* 19: 355–364 (1980)). A fragment from pAdDHFR containing the promoter and DHFR cDNA was inserted into pCMV6a to create pCMV9D.

EXAMPLE 4

Construction of a COS Cell Line Expressing $ETB_1$ Receptor Polypeptide

The mammalian cell expression vector, VCE40, is introduced into COS-7, monkey kidney cells by electroporation. The electroporated cells transiently expressed the native $ETB_1$ receptor polypeptide.

A monolayer of confluent COS-7 cells were rinsed once with calcium and magnesium free phosphate buffered saline (CMF-PBS). Five ml of trypsin/EDTA solution was added to the culture media to detach the cells from the solid support. The cells were incubated in the trypsin/EDTA solution at 37° C. until the cells detached. The composition of the trypsin/EDTA solution was: 1.6 g KCl, 32 g NaCl, 4 g glucose, 2.32 g sodium bicarbonate, 10 g trypsin, 0.4 g EDTA, 0.016 g Phenol red in a final volume of 4 L of water titrated to pH 7.0–7.1 with HCI.

Next, the cells were resuspended into a tube containing 5 mls 10% (v/v) fetal calf serum in DME with glutamine (from the University of California, San Francisco), 1.0M HEPES, to inhibit the trypsin enzymatic activity. The detached cells were centrifuged in a table-top centrifuge at 1,000 g for 3 minutes and then resuspended in PBS. This step was repeated twice. After the final centrifugation, the cells are resuspended at a concentration of $1\times10^7$ cells/ml in 10 mM HEPES/PBS. Two hundred and fifty μl of the cell suspension was added to the electroporation cuvette with 0.4 cm electrode gaps from BIORAD (Hercules, Calif., U.S.A.) with 10 μg of $pCM9DETB_1$.

The cells were electroporated in a BIORAD gene pulser apparatus, catalog no. 165–2076 with a capacitance extender, also from BIORAD (Hercules, Calif., U.S.A.), catalog no. 165–2087. The apparatus was set at 400 Volts and 250/μFd. The cells were pulsed at room temperature. After electroporation, the cells were vigorously pipetted to disperse the clumps of cells. Approximately, 1 ml of 10% (v/v) FCS in DME was added to the cuvette, and this cell suspension was plated onto a 100 mm plate with 10 ml of 10% (v/v) FCS in DME.

Expression of the native $ETB_1$ receptor polypeptide is determined by Western utilizing rabbit polyclonal antibodies which bind specifically to the following amino acid sequences (1) EEKQSCLKFKANDHG (SEQ ID NO: 10), (2) PRTISPPPCQGPIEIC (SEQ ID NO: 11), (3) DPNRCELLSFLL (SEQ ID NO: 12), and (4) SLKYNSIFIFC (SEQ ID NO: 13). Expression can also be confirmed by ligand binding assays, as described in Example 5.

After transfection, the cells are washed with PBS and released from the culture plates by scraping the cells into PBS containing 5 mM EDTA and a protease cocktail. The protease cocktail contains 0.5 mM PMSF, 5 μg/ml aprotinin, 5 μg/ml leupeptin, and 5 μg/ml pepstatin. Cells are harvested by centrifugation at 2,000 ×g for 4 minutes at 4° C. and resuspeded in 1 ml PBS-protease cocktail. The harvested cells are lysed by rapidly diluting the cells into 20 ml of ice-cold 20 mM HEPES buffer, pH 7.5 containing protease cocktail. The lysed cells are centrifuged at 30,000 g for 30 minutes. The pellet, containing the cell membranes, is separated from the aqueous phase, and then the pellet is resuspended in 50 mM HEPES, pH 7.5, 10 mM $MgCl_2$.

The cell membrane fraction is run on a 10% acrylamide SDS-PAGE gel. The gel is blotted overnight onto Immobilon-P (from Millipore, Bedford, Mass., U.S.A.) at 25 volts. The filter is blocked with 5% milk powder, 0.5 M NaCl, 20 mM Tris, pH 7.5, and 0. 1% Tween® 20 for 1 hour at room temperature.

The IgG fraction of the first antibody is diluted 1:100 (~1 μg/ml) into blocking solution. The filter is incubated in this solution for 1 hour at room temperature. Next, the filter is washed three times with 0.5 M NaCl, 20 mM Tris, pH 7.5, and 0. 1% Tween 20. The filter is incubated in the solution for ten minutes for each wash.

The second antibody, a goat anti-rabbit horse conjugated to horse radish peroxidase (Boehringer Mannheim, Cincinnati, Ohio, U.S.A.), is diluted 1:30,000 in blocking solution. The filter is incubated in this solution for 1 hour at room temperature. Next, the filter is washed three times with 0.5 M NaCl, 20 mM Tris, pH 7.5, and 0.1% Tween 20. The filter is incubated in the solution for ten minutes for each wash.

The bound antibodies are detected by ECL (enhanced chemiluminescence) using detection reagents by Amersham.

EXAMPLE 5

Construction of a CHO Cell Line Expressing $ETB_1$ Receptor Polypeptide

One of the most commonly used methods of introducing DNA into mammalian cells is to coprecipitate the DNA with calcium phosphate and present the mixture to cells. The specific procedure used to transfect Chinese Hamster Ovary (CHO) cells with the plasmid VCE 40 is as follows.

DG44 CHO cells were seeded at $7.1\times10^5$ cells per 60 mm dish in 10% fetal bovine serum (FBS) in Ham's F12. The cells were grown about 24 hours until the dishes were 80% confluent. On the day of the transfection the following DNA-calcium phosphate coprecipitate was prepared:

| | |
|---|---|
| VCE40 | 40.5 μl |
| TE[1] | 399.5 μl |
| 2x HBS[2] | 500 μl |
| 2 M $CaCl_2$[3] | 60 μl |

[1]TE = 10 mM Tris-HCl, 1 mM EDTA pH 8.0
[2]HBS = Hanks' balanced salts: 1.4 mM $Na_2HPO_4$, 10 mM KCl, 12 mM glucose, 275 mM NaCl, and 40 mM HEPES, pH 6.95.
[3]2 M $CaCl_2$ is diluted in 10 mM HEPES, pH 5.8.

The solution was mixed and incubated at room temperature for 30 minutes. Then, the medium was removed from the cells and 9 ml of fresh media was added to the dishes. The DNA-calcium phosphate coprecipitate was mixed by pipetting the solution and 1 ml of the DNA coprecipitate was added to each dish.

The cells were incubated with the DNA coprecipitate at 37° C. for 4 hours. The medium was removed from the cells and replaced with 2 ml of 20% (w/v) dimethyl sulfoxide (DMSO) in 1×HBS. After 2 minute incubation at room Temperature, 4 ml of serum-free Ham's F12 medium was added. The medium is removed and the cells were washed twice with 4 ml of serum-free Ham's F12 medium. Finally, 4 ml of 10% FBS in Ham's F12 medium was added, and the cells were incubated at 37° C. for 24 hours.

The medium was removed and 4 ml of the selective medium was added. The selective medium was composed of 10% dialyzed FBS in Ham's F12 (without hypoxanthine and thymidine), 10,000 U/L penicillin, 10 mg/L streptomycin, and 2.5 mg/L amphotericin B. The clones were picked and screened using a ligand binding assay.

The cells from the clone were plated with 10 ml medium in 100 mm plates. When the plates are ~90% confluent, the media is removed and the plates are rinsed with 5.0 ml of calcium and magnesium free PBS with 6 mM EDTA. Next, 5.0 ml of the PBS/EDTA medium is added to the plates and the medium is pipetted up and down to dislodge the cells from the plate. The medium with the cells is saved for assay. The plates are washed with 2.5 ml of the PBS/EDTA media and is added to the 5.0 ml of dislodged cells. Ten ml of binding buffer is added to the cells to dilute out the EDTA. The composition of the binding buffer is 25 mM HEPES, 150 mM NaCl, 5 mM $CaCl_2$, 1 mg/ml bovine serum albumin (BSA). The cells are centrifuged to pellet the cells and remove the supernatant. The cells are resuspended in 5.0 ml of binding buffer 100 μl of this solution containing cells and radioactive endothelin was added to 300 μl of binding buffer containing 0.1 nM of radioactive endothelin (either 1 or 3) from Amersham (Arlinton Heights, Ill., U.S.A). and varying concentrations of unlabeled endothelin from Bachem (Torrence, Calif., U.S.A). The recommended final concentrations of the unlabeled endothelin is 100 nM, 10 nM, 1 nM, and 100 pM. The sample is placed on a 0.24 cm glass fiber filter from Millipore and dried on a Millipore 1225 Sampling Manifold (cat. no. XX27–02550, Bedford, Mass., U.S.A.)

EXAMPLE 6

Construction of an Insect Cell $ETB_1$ Receptor Polypeptide Expression Vector The resulting XmaI/XbaI $ETB_1$ receptor polypeptide fragment from Example 2 was ligated with a EcoRV/XbaI fragment of $ETB_1$ receptor with the insect cell expression vector, pBacPAK9, from Clontech, Palo Alto, Calif., U.S.A. pBacPAK9 contains a polylinker so that the $ETB_1$ receptor coding sequence can be inserted after the polyhedrin promoter by digesting the pBacPAK9 with XmaI and EcoRV.

The resulting insect cell expression vector was named VCE 39. This vector was transformed into *E. coli* DH5α cells and deposited with the American Type Culture Collection (ATCC), Rockville, Md., U.S.A. The transformed cells were assigned accession no. 69321.

This expression vector is used as a transfer vector to construct a baculovirus containing the $ETB_1$ receptor polypeptide coding sequence. A description of such a vector is described below.

EXAMPLE 7

Construction of an Insect Cell Line Expressing $ETB_1$ Receptor Polypeptide

1.) The Production of a Recombinant Baculovirus

The transfer vector with the $KGF_{163}$ coding sequence and its signal peptide insert is transfected together with a mutant baculovirus into *Spodoptera frugiperda*, SF9 cells. The mutant baculovirus is a derivative of AcNPV that lacks a functional essential gene. This mutant baculovirus must recombine with the transfer vector to produce a viable baculovirus. To increase the number of recombinants, the mutant baculovirus was linearized with BsuI. In this regard, several BsuI sites were incorporated into the mutant baculovirus for this purpose. This mutant baculovirus is similar to the baculovirus described in Kitts et al., *Biotechniques* 14(5): 810–817 (1993).

A.) Preparation of Recombinant Baculovirus

First, $1\times10^6$ SF9 cells are seeded per well in a 6-well plate containing 2 ml of a complete TNMFH medium. The cells are incubated for at least 30 minutes at room temperature to allow the cells to attach to the plate. The complete TNMFH medium contained GRACE'S medium obtained from JRH Biosciences, Lenexa, Kans., U.S.A. and is supplemented with 10% (v/v) fetal bovine serum (56° C. heat inactivated for 30 minutes), 3% (w/v) Yeastolate (Difco, Detroit, Mich., U.S.A.), and I% (v/v) Fungi-BACT (Irvine Scientific, Santa Ana, Calif., U.S.A.).

For addition to each of the above wells, the following transfection mixture is initially separately prepared by first, adding 0.5 ml of GRACE'S medium containing no supplement into a sterile 1.5 ml eppendorf tube; next, adding 0.5 μg of linearized mutant baculovirus DNA and, approximately, 2–3 μg of the transfer vector containing the $KGF_{163}$ coding sequence and the signal peptide insert. This is approximately a 4:1 ratio of transfer vector to mutant baculovirus. Finally, the cationic liposome solution, BRL catalog #8282SA (from BRL, Gaithersburg, Md., U.S.A.) is mixed thoroughly, and 10 μl of this liposome solution were added to the baculovirus mixture. This transfection mixture is incubated at room temperature for 15 minutes.

Before the transfection mixture is added to the cells in the wells, the TNMFH medium is removed therefrom, and the cells are washed with 1–2 ml of GRACE'S medium without supplements. When the transfection mixture is finally prepared, as described above, all the medium is removed from the SF9 cells, and the transfection mixture is added dropwise to the cells. The 6-well plate is then covered with parafilm to reduce evaporation of the transfection mixture. The plate is rocked slowly at room temperature for approximately four hours on a Bellco®, catalog no. #774020020, Vineland, N.J., U.S.A., side/side rocking platform at setting 2.5.

After the incubation of the cells with the transfection mixture, 0.5 ml of complete TNMFH medium is added to the cells and the mixture is incubated at 27° C. in a humidified chamber (92%) for 48 hours. Thereafter, the medium containing recombinant baculovirus is removed from the cells and stored at 4° C. until the plaque assay for recombinant virus isolation is performed. This medium constitutes the primary source of the recombinant virus.

After the medium is removed from the cells, 2 ml of complete TNMFH is added to the cells, and the cells are further incubated in a humidified chamber (92%) at 27° C. for another 48–72 hours. This final step is performed to provide a back-up source of recombinant virus and to provide a visual record of the viral infection.

B.) Plaque Purification of the Recombinant Baculovirus

The recombinant KGF baculoviruses prepared as above were plaque-purified according to the following steps:

First, 4 ml of SF9 cells at 5×105 cells/ml in GRACE'S medium is plated on 60 mm LUX dishes (catalog #5220). The cells are incubated at room temperature for 20–30 minutes to allow the cells to adhere to the plate. In the meantime, the medium containing the primary source of recombinant virus is diluted into 2 ml of TNMFH medium at 1:10, 1:50, 1:100, and 1:200 dilutions. After the cells are allowed to adhere, the medium is aspirated from the adherent cells, and the various dilutions of the recombinant virus are added quickly so as not to allow the cells to dry. The cells are then incubated for 1 hour at 27° C. in a humidified chamber (92%).

Ten minutes before the incubation is complete, an agarose solution is prepared. A 2× concentration of GRACE'S medium supplemented as before is heated to 37° C. Only the amount used for the assay is heated; otherwise, proteins may precipitate upon repeated heating. When the 2× medium was warm, a 3% (w/v) Sea Plaque agarose mixture in water is melted in a microwave and immediately mixed 1:1 with the 2× medium. The agarose solution is then allowed to cool at room temperature for several minutes.

The viral medium is aspirated from the cells in the dishes by tilting the dishes slightly on the hood rim. The dishes are then drained for a few seconds and aspirated again to remove as much liquid as possible. This second aspiration step is included to reduce the likelihood of virus spreading and causing indistinct plaques. Six dishes or fewer are handled at a time to avoid drying the cells. The aspirated dishes are never left exposed with the lids off for more than a few seconds.

Next, 4 ml of the agarose solution are added to each dish and left undisturbed for 15 minutes. The agarose overlay is dried by lifting the lids to the side of the plate to permit the agarose to dry for approximately 25 minutes. Then, the dishes are covered with the lids, and the cells are incubated in a humidified chamber (92%) for 4 days at 27° C.

To facilitate visualization of the plaques, the dishes are stained with 2 ml per dish of 25% (w/v) Sea Plaque agarose in complete TNMFH medium with 0.01% (v/v) neutral red, from Sigma, St. Louis, Mo., U.S.A. The agarose overlay is dried at room temperature for about one hour with the lids on, before the dishes are returned to a humidified chamber (92%) at 27° C. for 3–4 hours. The neutral red dye is incorporated only by the viable cells.

When the plaques are well-resolved, 7 individual plugs are picked with a sterile Pasteur pipet and each is transferred to 1 ml of complete TNMFH. The plugs are incubated for 2 days at room temperature. The plugs were then vortexed, and the plaque assay was repeated with 50 μl of this solution.

C.) Expansion of the Plague Purified Baculovirus

To expand the viral titers, 3–4 plugs of each baculovirus clone from the second round of plaque purification are placed directly onto cultures of Sf9 cells. The cells are plated at $2.5\times10^5$/well in 6-well plates with 2.5 ml of complete TNMFH medium. The cells and virus were then incubated for approximately 4 hours at 27° C. in a humidified chamber (92%).

For the second round of expansion, all the virus from the 6-well plates are transferred to 10 cm dishes. The 10 cm dishes are plated with $7.5\times10^6$ cells in 7.5 ml of complete TNMFH media. The cells and virus are incubated for 48–72 hours at 27° C. in a humidified chamber (92%).

After this infection, the cells are thoroughly screened for any wild type virus contamination that appeared as infected cells containing occlusion bodies.

2.) Insect Cell Expression of an $ETB_1$ Receptor Polypeptide Coding Sequence

SF9 insect cells are infected with the recombinant baculovirus, as described in sections A–C, to provide a large amount of recombinant native $ETB_1$ receptor polypeptide for purification and analysis.

More specifically, SF9 cells are diluted to a cell density of $1\times10^6$ cells/ml in ISFM-7. The cells are seeded into either a 1 L or 2 L shake flask with 300 ml or 500 ml of medium, respectively. Virus from the second expansion (described in section C) was used to inoculate the cells at 10% (v/v) dilution. The cells and virus are shaken at approximately 131 rpm with the caps of the shake flasks are loosened to provide an adequate air supply. The cells are incubated at 27° C. for 48 hrs.

EXAMPLE 8

Identification of Endothelin Agonists and Antagonists

Construction of an phage library encoding random peptides is described in Devlin, W091/18980. Such a construction consists of (1) Producing Oligonucleotides Encoding Random Peptides;

(2) Creating a Shuttle Vector, Plasmid M13LP67, for Recombination with the Wild Type Phage; and (3) Production of Phage Encoding Random Peptides by Recombination.

Once the phage library is constructed, the library is screened using a $ETB_1$ receptor polypeptide. From the phage library, peptides with the desired binding properties can be assayed for their endothelin agonist or antagonist properties.

I. Producing Oligonucleotides Encoding Random Peptides

An oligonucleotide having the following structure was synthesized, and purified using methods known in the art, as described in Devlin, W091/18980: 5' CTTTCTATTCTCACTCCGCTGAA(NNS)$_{15}$CCGCCTCCACCTCCACC 3' (SEQ ID NO:14); and 5'GGC CGG TGG AGG TGG AGG CGG (iii)$_{15}$ TTC AGC GGA GTG AGA ATA GAA AGG - TAC 3' (SEQ ID NO: 15).

During the synthesis of $(NNS)_{15}$, a mixture consisting of equal amounts of the deoxynucleotides A, C and T, and about 30% more G was used for N, and an equal mixture of C and G for S. Deoxyinosine (i) was used because of its capacity to base pair with each of the four bases (A, G, C, and T) (J.F. Reidhaar-Olson et al., *Science*, (1988) 24:53). Alternatively, other base analogs may be used as described by J. Habener et al., *Proc Natl Acad Sci USA* (1988) 85:1735.

Immediately preceding the nucleotide sequence that encodes the random peptide sequence is a nucleotide sequence that encodes alanine and glutamic acid residues. These amino acids were included because they correspond to the first two amino terminal residues of the wild type mature gene III protein of M13, and thus may facilitate producing the fusion protein produced as described below.

Immediately following the random peptide sequence is a nucleotide sequence that encodes 6 proline residues. Thus, the oligonucleotide encodes the following amino acid sequence:

$H_2N$-Ala-Glu-$Xaal_{15}$-$Pro_6$ (SEQ ID NO:27)

Xaa denotes amino acids encoded by the random DNA sequence. As described below, the oligonucleotides were cloned into a derivative of M13 to produce a mature fusion protein having the above amino acid sequence, and following the proline residues, the entire wild type mature gene III.

II. Construction the Shuttle Vector Plasmid M13LP67, for Recombination with the Wild Type Phage The plasmid M13LP67 was used to express the random peptide/gene III fusion protein construct. M13LP67 was derived from M13 mpl9.

Briefly, Ml3mpl9 was altered in two ways. The first alteration consisted of inserting the marker gene, β-lactamase, into the polylinker region of the virion. This consisted of obtaining the gene by PCR amplification from the plasmid pAc5. The oligonucleotide primers that were annealed to the pAc5 template hare the following sequence:

5' GCT GCC CGA GAG ATC TGT ATA TAT GAG TAA ACT TGG 3' (SEQ ID NO:16)

5' GCA GGC TCG GGA ATT CGG GAA ATG TGC GCG GAA CCC 3' (SEQ ID NO: 17)

Amplified copies of the β-lactamase gene were digested with the restriction enzymes BglII and EcoRl, and the replicative form of the modified M13 mp19 was digested with BamHI and EcoRl. The desired fragments were purified by gel electrophoresis, ligated, and transformed into *E. coli* strain DH5 alpha (BRL). *E. coli* transformed with phage that carried the insert were selected on ampicillin plates. The phage so produced were termed JD32.

The plasmid form of the phage, pJD32 (M13mp19Amp'), was mutagenized so that two restriction sites, EagI and KpnI, were introduced into gene III without altering the amino acids encoded in this region. The restriction sites were introduced using standard PCR in vitro mutagenesis techniques as described by M. Innis et al. in "PCR Protocols—A Guide to Methods and Applications" (1990), Academic Press, Inc.

The KpnI site was constructed by converting the sequence, TGTTCC, at position 1611 to GGTACC. The two oligonucleotides used to effect the mutagenesis have the following sequence:

LP159: AAACTTCCTCATGAAAAAGTC (SEQ ID NO:18)

LP162: AGAATAGAAAGGTACCACTAAAGGA (SEQ ID NO: 19).

To construct the EagI restriction site, the sequence at position 1631 of pJD32, CCGCTG, was changed to CGGCCG using the following two oligonucleotides:

LP160: TTT AGT GGT ACC TTT CTA TTC TCA CTC GGC CGA AAC

TGT (SEQ ID NO:25)

LP161: AAA GCG CAG TCT CTG AAT TTA CCG (SEQ ID NO:26)

More specifically, the PCR products obtained using the primers LP159, LP162 and LP160 and LP161 were digested with BspHI and KpnI, and KpnI and AlwNI, respectively. These were ligated with T4 ligase to M13mpl9 previously cut with BspHI and AlwNI to yield M13mpLP66. This vector contains the desired EagI and KpnI restriction sites, but lacks the ampicillin resistance gene, β-lactamase. Thus, the vector M13mpLP67, which contains the EagI and KpnI restriction sites and β-lactamase was produced by removing the β-lactamase sequences from pJD32 by digesting the vector with XbaI and EcoRI. The β-lactamase gene was then inserted into the polylinker region of M13mpLP66 which was previously digested with XbaI and EcoRI. Subsequent ligation with T4 ligase produced M13mpLP67, which was used to generate the random peptide library. Schematics of the construction of M13mpLP67 are shown in Devlin et al., PCT W091/18980.

Production of Phage Encoding Random Peptides

To produce phage having DNA sequences that encode random peptide sequences, M13LP67 was digested with EagI and KpnI, and ligated to the oligonucleotides produced as described in Example 1 above. The ligation mixture consisted of digested M13LP67 DNA at 45 ng/$\mu$L, a 5-fold molar excess of oligonucleotides, 3.6 U/$\mu$L of T4 ligase (New England Biolabs), 25 mM Tris-HCI, pH 7.8, 10 mM $MgC'_2$, 2 mM DTT, 0.4 mM ATP, and 0.1 mg/ml BSA. Prior to being added to the ligation mixture, the individual oligonucleotides were combined and heated to 95° C. for 5 minutes, and subsequently cooled to room temperature in 15 $\mu$L aliquots. Next, the ligation mixture was incubated for 4 hours at room temperature and subsequently overnight at 15° C. This mixture was then electroporated into *E. coli* as described below.

M13LP67 DNA was electroporated into H249 cells prepared essentially as described by W. Dower et al., *Nuc Acids Res* (1988) 16:6127. H249 cells are a recA, sup°, F' $kan^R$ derivative of MM294. Briefly, $4\times10^9$ H249 cells and 1 $\mu$g of M13LP67 DNA were combined in 85 $\mu$L of a low conductivity solution consisting of 1 mM HEPES. The cell/ Ml3LP67DNA mixture was positioned in a chilled 0.56 mm gap electrode of a BTX electroporation device (BTX Corp.) and subjected to a 5 millisecond pulse of 560 volts.

Immediately following electroporation, the cells were removed from the electrode assembly, mixed with fresh H249 lawn cells, and plated at a density of about $2\times10^5$ plaques per 400 $cm^2$ plate. The next day phage from each plate were eluted with 30 ml of fresh media, PEG precipitated, resuspended in 20% glycerol, and stored frozen at −70° C. About $2.8\times10^7$ plaques were harvested and several hundred analyzed to determine the approximate number that harbor random peptide sequences. Using the polymerase chain reaction to amplify DNA in the region that encodes the random peptide sequence, it was determined that about 50–90% of the phage contained a 69 base pair insert at the 5' end of gene III. This confirmed the presence of the oligonucleotides that encode the random peptides sequences. The PCR reaction was conducted using standard techniques and with the following oligonucleotides:

5' TCGAAAGCAAGCTGATAAACCG 3' (SEQ ID NO:20)

5' ACAGACAGCCCTCATAGTTAGCG 3' (SEQ ID NO:21)

The reaction was run for 40 cycles, after which the products were resolved by electrophoresis in a 2% agarose gel. Based on these results, it was calculated that phage from the $2.8\times10^7$ plaques encode about $2\times10^7$ different random amino acid sequences.

Panning for Endothelin Agonists and Antagonists

Peptides having an affinity for $ETB_1$ receptor are identified as follows:

1.) 15mer phage ($2.5\times10^{10}$) prepared as described above are selected by coincubation with $10^6$ Sf9 cells expressing native $ETB_1$, (See Example 7) on the second day after infection. The coincubation is at room temperature for 60 minutes in Grace's medium with 2% nonfat milk. Binding phage are eluted with 6M urea (pH 2.2), the pH neutralized by adding 2M Tris-HCI, and assayed. The phage are amplified on solid agar plates as plaques, eluted with Tris-buffered saline, and precipitated with polyethylene glycol.

2.) The phage resulting from round 1 are reselected on CHO cells expressing the native $ETB_1$ (See Example 5) on second day 2 after plating the cells at a density of $7.1\times10^5$, using $3.1\times10^{11}$ phage on in DMEM with 2% nonfat milk and 10 mM HEPES. The phage are bound, eluted, assayed, and amplified as described in round 1.

3.) The phage selected in round 2 are reselected on Sf9 cells expressing the native $ETB_1$ receptor on day 2 post-infection as described for round 1 ($2.8\times10^{10}$ phage on $10^6$ Sf9 cells). Sample phage from the urea eluate are cloned, and their DNAs are isolated and sequenced.

Once the amino acid sequence of the putative agonists and antagonists is determined, synthetic oligopeptides can be produced and their signal transduction activity can be assayed by, for example, Amersham's inositol 1,4,5-trisphosphate assay system (Arlington Heights, Ill., U.S.A.).

CHO cells expressing the $ETB_1$ receptor polypeptide (Example 5) are plated at a density of $1\times10^5$ cells/well in a 12-well plate. The cells are cultured for 2 days, and then, the cells are washed twice with PBS containing 0.2% BSA. Next, the cells are incubated in the same medium for 30 minutes at 37° C. The medium on the cells is changed to PBS containing 0.2% BSA and 10 mM LiCl, and the cells are incubated for another 30 minutes at 37° C.

Signal transduction is induced by changing the medium of the cells to PBS containing 0.2% BSA, 10 mM LiCl, and the desired concentration of the oligopeptide, as determined by the screening. The cells are incubated in this medium for 5 minutes and then the media is removed from the cells. Next, 0.2 volumes ice-cold 20% (v/v) perchloric acid (PCA) is added to the cells to quench the stimulation and to prepare the cells for the inositol phosphate assay. The cells are incubated on ice in PCA for 20 minutes. At the beginning of the incubation, the cells are dislodged from the plate with a rubber policeman. After the incubation, the cells are removed from the plate and centrifuged at 2,000×g for 15 minutes at 4° C. The supernatants are removed and titrated to pH 7.5 with 10 N KOH and kept on ice. The solution is centrifuged at 2,000×g for 15 minutes at 4° C. to remove the precipitate. The supernatant is then assayed to determine the amount of inositol trisphosphate present.

Amersham provides a kit containing the reagents for an inositol triphosphate competition assay. With the kit, an inositol 1,4,5-trisphosphate binding protein is provided, which cross-reacts with inositol 1,3,4,5-tetrakisphophate less than 10% and less than 1% with other inositol phosphates. The assay measures that amount of inositol triphosphate that competes for the binding protein with the radioactive labeled triphosphate.

1.) Preparing the Standard

First all the reagents to thaw at 2–8° C. and then mix thoroughly. As this is occurring, label 8 poypropylene tubes (12×75 mm) "0.19," "0.38," "0.76," "1.5," "3.1," 6.2, "12.5," and "25 pmol." Pipette 1.5 ml of water into the tube marked "25 pmol." Into the remaining marked standard tubes pipette 500 $\mu$l of water. Next, into the marked "25 pmol" tube, add exactly 100 $\mu$l of the standard solution (3 nmol D-myo-inositol 1,4,5-trisphosphate in water). Mix the solution completely. Transfer 500 μl of the 25 pmol solution to the 12.5 pmol tube, and vortex the solution throughly. Repeat this 1:2 dilution succesively with the remaining tubes. These working standards should be prepared immediately before each assay and not re-used. The standard solution from the kit should be recapped after use and immediately stored at −15° C. to −30° C.

2.) Assay Protocol

First label duplicate polypropylene tubes (10×55 mm) "TC" for total counts; "NSB" for non-specific binding; "$B_0$" for zero standards; "0.19," "0.38," "0.76," "1.5," "3.1," 6.2 "12.5 " and "25 " pmol for the standards; and whatever is desired for the samples. Next, pipette into all the tubes 100 μl of the assay buffer (0.1M Tris buffer pH 9.0, 4 mM EDTA and 4 mg/mIl bovine serum albumin (BSA)). Into the $B_O$ and TC tubes, 100 μl and 200 μl, respectively deionized water is added. Then, starting with the most dilute solution, pipette 100 μl of each of the standard solutions, described above, into the appropriately labelled tubes. Use a new pipette tip for each standard solution. Add into the NSB tubes, 100 μl of stock standard solution (3 nmol D-myo-inositol 1,4,5-trisphosphate in water). One hundred microliters of the samples should be added to the appriopriate sample tubes. Use a new pipette tip for each sample.

One hundred microliters of first the tracer (~1.0 μCi or ~37kBq of D-nyo-[$^3$H]inositol 1,4,5-trisphosphate in 1:1 (v/v) water:ethanol) and then binding protein is added to all the tubes. All the tubes are vortexed to mix all the contents throughly and then incubated for 15 minutes on ice. Then, the binding protein is isolated by the centrifugation procedure below.

All the tubes, except those labelled "TC", are centrifuged at 2,000×g for at least 10 minutes at 4° C. After centrifugation, the tubes are carefully placed into a suitable decantation rack and the supernatant is poured off and discarded. The tubes are kept inverted and placed on absorbent tissues and allowed to drain for 2 minutes. Next, the rims of the inverted tubes are firmly blotted on the tissue to remove any adhering droplets of liquid, and the inside of the tubes are carefully swapped for the same reason. This is done carefully to avoid disturbing the pellet at the bottom of the tube.

To each tube, 200 μt of water is added to resuspend the pellet except the "TC" labelled tubes. The tube is vortexed to mix the solution throughly. Then, 2 ml of scintillation fluid is added to the resuspended pellet. Before measuring the radioactivity of each sample for four minutes in a 0-scintillation counter, the samples are capped and mixed throughly.

EXAMPLE 9

Purification of $ETB_1$ Receptor Polypeptides from Nucleic Acids

Membrane preparation for endothelin ligand binding assay using COS-7 or CHO cells transfected with VCE 40. See Examples 4 and 5. COS-7 cells, for example, are grown in 245 mm×245 mm tissue culture plates and transfected according to the protocol in Example 4 with 30 μg of VCE 40 plasmid DNA. After two days, the cells are washed with PBS and released from the culture plates by scraping the cells into PBS containing 5 mM EDTA and a protease cocktail. The protease cocktail contains 0.5 mM PMSF, 5 μg/ml aprotinin, 5 μg/ml leupeptin, and 5 μg/ml pepstatin. Cells are harvested by centrifugation 2,500×g for 5 minutes at 4° C., and resuspended in 1 ml of the PBS-protease cocktail. The harvested cells are lysed by rapidly diluting the cells into 20 ml of ice-cold 20 mM HEPES buffer, pH 7.5 containing protease cocktail. The lysed cells are centrifuged at 30,000 g for 30 minutes. The pellet, containing the cell membranes, is separated from the aqueous phase, and then the pellet is resuspended in 50 mM HEPES, pH 7.5, 10 mM $MgCl_2$. The membranes can be frozen at −70° C. for future use.

Deposit Information:

The following materials were deposited with the American Type Culture Collection:

| Name | Deposit Date | Accession No. |
|---|---|---|
| *Escherichia coli* DH5α, VCE 39 | 4 June 1993 | 69321 |
| *Escherichia coli* DH5α, VCE 40 | 4 June 1993 | 69322 |
| Phage Library 7.1 in M13LP67 | | 40828 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

What is claimed:

1. A method of screening for a test candidate that binds an endothelin $B_1$ ($ETB_1$) receptor polypeptide and modulates signal transduction activity comprising:

(a) providing a host cell transformed with a DNA encoding endothelin $B_1$, receptor ($ETB_1$) polypeptide having SEQ ID NO:1;

(b) exposing said cell to said test candidate; and (c) measuring endothelin $B_1$ receptor signal transduction activity.

2. A method of screening for a test candidate that binds an endothelin $B_1$ ($ETB_1$) receptor polypeptide and modulates signal transduction activity comprising:

(a) providing a host cell transformed with a DNA encoding endothelin B, receptor ($ETB_1$) polypeptide having SEQ ID NO:1;

(b) exposing said cell to said test candidate;

(c) lysing said cell; and (d) measuring endothelin $B_1$ receptor signal transduction activity.

* * * * *